United States Patent [19]
McInally et al.

[11] Patent Number: 4,831,070
[45] Date of Patent: May 16, 1989

[54] MOLDABLE ELASTOMERIC PRESSURE SENSITIVE ADHESIVES

[75] Inventors: Linda J. McInally; John T. Woodard, both of Midland, Mich.

[73] Assignee: Dow Corning Corporation, Midland, Mich.

[21] Appl. No.: 115,807

[22] Filed: Nov. 2, 1987

[51] Int. Cl.$^4$ .............................................. C08K 5/54
[52] U.S. Cl. .................................. 524/267; 524/265; 524/266; 524/588; 524/730; 524/731; 524/860; 525/477; 525/100; 525/105; 525/106; 525/453; 528/15; 528/34; 528/18; 528/19; 528/901
[58] Field of Search ............... 525/477, 100, 105, 106, 525/453; 524/860, 265, 266, 588, 730, 731, 267; 528/15, 34, 18, 19, 901

[56] References Cited

U.S. PATENT DOCUMENTS

| | | | |
|---|---|---|---|
| 2,736,721 | 2/1956 | Dexter | 260/42 |
| 2,814,601 | 11/1957 | Currie et al. | 260/29.1 |
| 3,373,745 | 3/1968 | Benfield et al. | 128/283 |
| 3,527,659 | 9/1970 | Keil | 117/145 |
| 4,204,540 | 5/1980 | Cilento et al. | 128/283 |
| 4,255,316 | 3/1981 | Blizzard | 260/37 SB |
| 4,584,355 | 4/1986 | Blizzard et al. | 525/477 |
| 4,585,836 | 4/1986 | Homan et al. | 525/477 |
| 4,591,622 | 5/1986 | Blizzard et al. | 525/477 |
| 4,623,593 | 11/1986 | Baier et al. | 428/447 |

FOREIGN PATENT DOCUMENTS 711756 6/1965 Canada.
1343252 1/1974 United Kingdom.

OTHER PUBLICATIONS

"Silastic(R) 382 Medical Grade Elastomer" Bulletin: 51-437B, Dow Corning Corporation, Midland, MI, 4 pages (Jun., 1983).

"Dow Corning(R) Medical Adhesive B-New Formula", Bulletin: 51-059, Dow Corning Corporation, Midland, MI, 2 pages (Aug., 1971).

"Dow Corning Silicone Adhesive Data—Dow Corning 269 and 274 Adhesives", Bulletin: 02-006, Dow Corning Corporation, Midland, MI, 2 pages (Mar. 1963).

"Dow Corning(R) 355 Medical Adhesive", Bulletin: 51-248A, Dow Corning Corporation, Midland, MI, 2 pages (Feb. 1979).

Primary Examiner—Melvyn I. Marquis
Attorney, Agent, or Firm—Susan M. Cornwall

[57] ABSTRACT

A composition and method for forming elastomeric pressure sensitive adhesives comprising a mixture of (A) a xylene-soluble resin copolymer of 0.6 to 0.9 triorganosiloxy units per $SiO_{4/2}$ unit and having less than 0.7 weight % silicon-bonded hydroxyl units. (B) a polydiorganosiloxane fluid endcapped with silicon-bonded hydroxyl groups and having a viscosity of from about 50 to 300,000 cP. at 25° C., an organosilicon compound containing an average of more than two silicon-bonded alkoxy groups per molecule, and a condensation catalyst. The cured elastomeric pressure sensitive adhesives formed from these compositions are useful as medical adhesives, such as those used for ostomy seals.

23 Claims, No Drawings

MOLDABLE ELASTOMERIC PRESSURE SENSITIVE ADHESIVES

BACKGROUND OF THE INVENTION

The present invention relates to elastomeric silicone pressure sensitive adhesive compositions and their preparation. More particularly, the invention relates to solventless, moldable compositions which can be molded and cured at room temperature and which are useful for making medical adhesives, e.g. those used for sealing ostomy appliances.

Various silicone pressure sensitive adhesive (PSA) compositions, e.g. those disclosed in U.S. Pat. Nos. 2,814,601 and 2,736,721 and Great Britain Pat. No. 1,343,252, are known in the art. U.S. Pat. No. 2,814,601 to Currie, et al., describes silicone pressure sensitive adhesives composed essentially of (1) a benzene soluble resin copolymer of $SiO_2$ units and $R_3SiO_{0.5}$ units and (2) hydroxyl end-blocked diorganopolysiloxane fluid of from 5,000 to less than 1,000,000 cs viscosity at 25° C. When the compositions are to form adhesives which will give a permanent bond, Currie teaches that it is necessary to include an alkoxy polysilicate or a hydrogen bearing siloxane as a crosslinking agent.

U.S. Pat. No. 2,736,721 to Dexter discloses adhesives which are formed from a mixture of a benzene soluble resin copolymer and a diorganopolysiloxane having a viscosity of at least 1,000,000 cs. at 25° C. Dexter mentions that catalysts such as metal salts of carboxylic acids and alkoxy silanes may be added to the mixture, if desired.

Great Britain Pat. No. 1,343,252, discloses a process for preparing a pressure sensitive adhesive comprising mixing a curable composition comprising (a) an organopolysiloxane resin, (b) a diorganopolysiloxane polymer terminated at each end by a hydroxyl group and having a viscosity of $10^2$ to $10^7$ cP at 25° C., and (c) an organic peroxy compound with an organic diluent, heating the mixture for a time sufficient to remove the bulk of the diluent and then heating the residue at 80°–200° C. for at least 10 minutes.

Canadian Pat. No. 711,756 to Pail discloses an organosiloxane pressure sensitive adhesive composition prepared by heating a mixture of (1) a benzene soluble resin copolymer, (2) a hydroxy endblocked diorganopolysiloxane fluid having a viscosity in the range of 100 to 100,000 cs. at 25° C. and (3) an aliphatic organic amino compound above 100° C.

U.S. Pat. Nos. 4,591,622 and 4,584,355 to Blizzard, et al., and U.S. Pat. No. 4,585,836 to Homan, et al., disclose silicone pressure sensitive adhesives formed by condensing a benzene-soluble resin copolymer which contains silicon-bonded hydroxyl radicals and a polydiorganosiloxane having a viscosity of from 100 cP to 30,000,000 cP at 25° C. and containing hydrolyzable endblocking radicals with a sufficient amount of endblocking agent containing endblocking triorganosilyl units such as hexamethyldisilazane.

U.S. Pat. No. 4,255,316 to Blizzard describes ceramifiable silicone adhesives consisting of (I) a silicone pressure sensitive adhesive consisting of (A) a polydiorganosiloxane fluid having the average formula $YO(R_2SiO)_nY$ and having a viscosity of from 1 to 1000 pascal-seconds at 25° C. and (B) a xylene soluble resin copolymer and (II) a volatile free ceramifiable filler. Y denotes an oxygen-bonded terminating radical such as H. The resin copolymer may be treated with a suitable silylating agent, such as hexamethyldisilazane to reduce the hydroxyl content of the copolymer to less than 1 percent by weight. The composition may also contain a curing agent such as stannous octoate when (A) bears $\equiv SiOH$ endgroups.

A recent patent to Baier, et al., U.S. Pat. No. 4,623,593, discloses a method of making self-adhesive polymer compositions by curing polymers while selected surfaces are in contact with a cross-linking inhibition agents. In Baier's Example 5, a cross-linking inhibition agent was applied to selected surfaces of a mold and the mold was packed with "SILASTIC ® 382", and cured to create a polymer body with a tacky surface. SILASTIC ® 382 Medical Grade Elastomer (obtained from Dow Corning Corporation, Midland, MI) is a two-component silicone product consisting of an elastomeric base composed of polydimethylsiloxane and a silica filler and the catalyst, stannous octoate.

Silicone-containing pressure sensitive adhesive materials which have been disclosed as being useful for sealing ostomy appliances can be found, for example, in U.S. Pat. No. 4,204,540 to Cilento, et al., which describes the mixture of a pressure sensitive adhesive component, mineral oil, and hydrocolloid gums or cohesive strengthening agents or a mixture of hydrocolloid gums and cohesive strengthening agents. Although Cilento, et al., prefer polyisobutylenes as the pressure sensitive adhesive component, they suggest silicone rubber as the pressure sensitive adhesive component, but do not further describe the silicone rubber composition.

Other silicone-based adhesives which can be used for medical purposes are sold by Dow Corning Corporation, Midland, MI, as DOW CORNING ® Medical Adhesive B and 355 Medical Adhesive. The products consists of a polysiloxane polymer dissolved in fluorocarbon propellant, Medical Adhesive B being supplied in an aerosol container.

U.S. Pat. No. 3,373,745 to Benfield, et al. discloses the use of "DOW CORNING ® Adhesive 269 . . . or 274" for adhering an ostomy bag to the body. DOW CORNING ® Adhesives 269 and 274 were pressure sensitive silicone adhesives which were available from Dow Corning Corporation in Midland, MI.

SUMMARY OF THE INVENTION

Even in view of the extensive disclosure of silicone-based pressure sensitive adhesives, there remains a need for the improved compositions of this invention which form silicone elastomeric pressure sensitive adhesives that (1) have an adequately low working viscosity so that the composition can be easily molded at room temperature, (2) have a high solids (non-volatile) content for minimal bubbling in the cured product, (3) can be cured at room temperature, (4) can be made of medically-acceptable ingredients, (5) can be formulated to provide wet tack as well as dry tack, (6) cure to a product having good shelf aging properties, and (7) will not disintegrate under wet conditions.

This invention relates to a composition for forming elastomeric pressure sensitive adhesives comprising a mixture of a xylene-soluble resin copolymer, a hydroxy-endblocked polydiorganosiloxane fluid, an organosilicon compound containing an average of more than two silicon-bonded alkoxy groups per molecule, and a condensation catalyst. The invention also relates to the cured elastomeric pressure sensitive adhesives formed from these compositions, the method of making the cured elastomeric pressure sensitive adhesives, and their use as medical adhesives, such as those used for ostomy seals.

DETAILED DESCRIPTION OF THE INVENTION

Specifically, this invention relates to a moldable composition for forming elastomeric pressure sensitive adhesives comprising a homogeneous mixture of (A) 50 to 70 parts by weight of a xylene-soluble resin copolymer consisting essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than about 0.7 weight % silicon-bonded hydroxyl units, said resin copolymer containing substantially no volatile components, (B) from 30 to 50 parts by weight of a polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity so that the elastomeric pressure sensitive adhesive composition has a plasticity of less than $150 \times 10^{-3}$ inches at 25° C. without the addition of organic solvents, the total of resin copolymer (A) and polydiorganosiloxane (B) being 100 parts by weight, (C) an alkoxy-containing organosilicon compound having an average of more than two silicon-bonded alkoxy units per molecule employed from about 0.35 to about 2 parts by weight, and (D) a condensation catalyst employed in an amount from about 0.5 to 13 parts by weight.

The elastomeric pressure sensitive adhesive compositions are made in accordance with the present invention using from 50 to 70 parts by weight of resin copolymer (A) and from 30 to 50 parts by weight of polydiorganosiloxane (B), the total of resin copolymer (A) and polydiorganosiloxane (B) being 100 parts by weight. For purposes of forming an ostomy seal, more preferred compositions employ from 58 to 62 parts by weight of resin copolymer (A) and 38 to 42 parts by weight of polydiorganosiloxane (B). Most preferably, resin copolymer (A) is employed at 60 parts by weight and polydiorganosiloxane fluid (B) at 40 parts by weight. When resin copolymer (A) is employed at amounts between about 66 and 70 percent, the compositions may require the addition of organic tackifiers to achieve the desired physical properties. Organic tackifiers are discussed further below.

Resin copolymer (A) consists essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit and has less than about 0.7 weight % silicon-bonded hydroxyl units, and preferably less than 0.33 weight %. Each R denotes, independently, a monovalent hydrocarbon radical having from 1 to 6 inclusive carbon atoms, such as methyl ("Me"), ethyl, propyl, isopropyl, hexyl, cyclohexyl, vinyl ("Vi"), allyl, propenyl and phenyl ("Ph"). The R radicals may be the same or different, but at least 90 percent, and preferably 100 percent, of the R radicals are methyl radicals.

Resin copolymer (A) is a known material in the organosilicon art and is a solid, xylene-soluble, resinous material which is prepared in organic solvent solution and treated with an endblocking agent, as discussed below. Typical solvents that are used to dissolve resin copolymer (A) include benzene, toluene, xylene, methylene chloride, perchlorethylene and naphtha mineral spirits.

Resin copolymer (A) may be prepared by first preparing an untreated resin copolymer according to Daudt, et al., U.S. Pat. No. 2,676,182, and, thereafter, treating an organic solvent solution of the untreated resin copolymer with a suitable endblocking agent to reduce the amount of silicon-bonded hydroxyl units to less than about 0.7 weight % and, more preferably, to less than 0.33 weight %. In Daudt, et al., a silica hydrosol is treated at low pH with a source of $RF_3RSiO_{\frac{1}{2}}$ siloxane units, such as hexaorganodisiloxane, such as $MeF_3RSiOSiMeF_3R$, $ViMeF_2RSiOSiMeF_2RVi$, or $MeViPhSiOSiPhViMe$, or triorganochlorosilane, such as $MeF_3RSiCl$, $MeF_2RViSiCl$, or $MeViPhSiCl$. Alternatively, the untreated resin copolymer may be prepared by cohydrolyzing and condensing a mixture of suitable hydrolyzable, triorganosubstituted-silanes and hydrolyzable silanes free of R radicals.

The mole ratio of $R_3SiO_{\frac{1}{2}}$ and $SiO_{4/2}$ siloxane units can be determined simply from a knowledge of the identity of the R radicals in the $R_3SiO_{\frac{1}{2}}$ siloxane units and the percent carbon analysis of the resin copolymer. In a preferred resin copolymer consisting of a mol ratio of from 0.6 to $0.9Me_3SiO_{\frac{1}{2}}$ siloxane units for every $SiO_{4/2}$ siloxane unit, the carbon analysis has a value of from 19.8 to 24.4 percent by weight.

Treating an organic solvent solution of the untreated resin copolymer to reduce the silicon-bonded hydroxyl content may be done with a sufficient amount of at least one organosilicon endblocking agent capable of generating an end-blocking triorganosilyl unit. Endblocking agents capable of providing endblocking triorganosilyl units are commonly employed as silylating agents and a wide variety of such agents are known and are disclosed in U.S. Pat. Nos. 4,584,355 and 4,591,622 to Blizzard, et al. and U.S. Pat. No. 4,585,836 to Homan, et al. which are hereby incorporated by reference. A single endblocking agent such as hexamethyldisilazane can be employed or a mixture of such agents such as hexamethyldisilazane and sym-tetramethyldivinyldisilazane can be employed. A number of methods are known in the art for determining silicon-bonded hydroxyl content.

The procedure for treating the resin copolymer may be simply to mix the endblocking agent with a solvent solution of the resin copolymer and allowing the by-products to be removed. Preferably, an acid catalyst is added and the mixture is heated to reflux conditions for a few hours. It is preferred to treat resin copolymer (A) before mixing with polydiorganosiloxane fluid (B).

Resin copolymer (A) may be a blend of the treated (low silanol) resin copolymer and small amounts of the untreated resin copolymer, however, the partial substitution of untreated resin copolymer for treated resin copolymer results in a reduction in tack and adhesion. Amounts up to about 10% by weight of the composition of untreated resin copolymer are acceptable.

Polydiorganosiloxane fluid (B) has the average formula $HO(R'_2SiO)_nH$ wherein each R' denotes, independently, a monovalent hydrocarbon or halohydrocarbon radical having from 1 to 6 inclusive carbon atoms such as methyl, phenyl, vinyl, chloromethyl, chloropropyl, 1-chloro, -2-methylpropyl, 3,3,3-trifluoropropyl and $F_3C(CH_2)_5$. The R' radicals may be the same or different, but preferably, R' is a methyl radical. The polydiorganosiloxane must have a viscosity such that the elastomeric pressure sensitive adhesive composition has a plasticity of less than $150 \times 10^{-3}$ inches 23° C. or 150 "plasticity units". Preferably, the elastomeric pressure sensitive adhesive composition has a plasticity between 30 and 100 plasticity units at 23° C. and, more preferably, a plasticity between 30 and 65 plasticity units at 23° C. Plasticity may be measured using the ASTM D926 procedure. Generally, suitable fluids for this invention are those, e.g., having a viscosity of less than 300,000 cP. at 25° C. Preferably, polydiorganosiloxane fluid (B) has a viscosity of from 50 to 5000 cP. at 25° C. and more preferably, from 50 to 100 cP. For example, when a polydiorganosiloxane fluid (B) having a viscosity of about 70 cP. is used in a composition of 60 weight % resin copolymer (A) and 40 weight % polydiorganosiloxane fluid (B), the plasticity is about 40–55 plasticity units, and if for a similar composition, a polydiorganosiloxane fluid (B) having a viscosity of about 2000 cP. is used, the resulting plasticity is about 60. Polydiorganosiloxane fluids are well known in the organosilicon polymer art and their preparation needs no further comment.

Organosilicon compound (C) is a crosslinking compound having an average of more than two silicon-bonded alkoxy units per molecule. Such crosslinking compounds are known in the art. Suitable organosilicon compounds are silanes of the formula $(R''O)_3SiR'''$, orthosilicates of the formula $(R''O)_4Si$, or polymers or mixtures thereof where R'' is selected from monovalent hydrocarbon and halogenated hydrocarbon radicals having 6 carbons or less and radicals of the formula —CH$_2$CH$_2$OR'''' where R'''' is methyl, ethyl, propyl, butyl, amyl, or hexyl, both straight and branched chains and where R''' is hydrogen or any monovalent hydrocarbon or halogenated hydrocarbon radical having 6 carbons or less. Each of the R'', R''', and R'''' radicals may be the same or different. The composition can tolerate compounds having less than three alkoxy units per molecule, however, it is preferred that the organosilicon compounds used have at least three alkoxy units per molecule and, as stated, the average must be greater than two alkoxy units per molecule. It is preferred that both R'' and R''' are hydrocarbon radicals of less than 6 carbon atoms. It is most preferred that R'' is a hydrocarbon of 3 or less carbon atoms. Examples of suitable organosilicon compounds are methyltrimethoxysilane, tetramethoxysilane, N-propyl-orthosilicate, ethylorthosilicate, methylpolysilicates, ethylpolysilicates, propylpolysilicates, and butylpolysilicates. Preferred organosilicon compounds are ethylpolysilicate and N-propylorthosilicate.

Organosilicon compound (C) may be employed from about 0.35 to about 2 weight percent based of the total weight of the resin copolymer (A) and the polydiorganosiloxane (B). Preferably, organosilicon compound (C) is employed from about 0.67 to about 1.33 weight percent based on the total weight of the resin copolymer (A) and the polydiorganosiloxane fluid (B).

Condensation catalyst (D) may be selected from the group consisting of metal salts of carboxylic acids, such as zinc octoate, lead-2-ethyl hexoate, lead naphthenates, dibutylditindiacetate, dibutyltindilactate, stannous octoate, zinc napthanate, and ferrous octoate. Preferably, condensation catalyst (D) is stannous octoate. The catalyst may be employed in amounts from 0.5 to 13 weight percent based on the total weight of the resin copolymer (A) and the polydiorganosiloxane fluid (B). Preferably, catalyst (D) is employed at about 1 weight percent based on the total weight of the resin copolymer (A) and the polydiorganosiloxane fluid (B).

The composition may further include a trimethyl-endblocked polydimethylsiloxane fluid. The fluid can be employed to decrease the viscosity of the resulting composition. If a trimethyl-endblocked polydimethylsiloxane is employed, preferably it has a viscosity ranging from about 10 cSt. to about 1000 cSt. and more preferably the viscosity is about 100 cSt. The trimethyl-endblocked polydimethylsiloxane may generally be used in an amount up to about 15 weight percent of the total weight of the resin copolymer (A) and the polydiorganosiloxane fluid (B), and more preferably is used in amount from 3 to 6 weight percent.

Organic solvents may be added to the compositions, however, large quantities of solvents should be avoided when molding a body of substantial thickness since the evaporation of the solvents upon curing could result in bubbling in the cured product, which may be undesirable.

The compositions may also be blended with other materials that are known in the pressure sensitive adhesive art, such as plasticizers, co-solvents, or other silicone or organic pressure sensitive adhesive materials. Examples of organic pressure sensitive adhesive materials include natural rubber, styrene-butadiene rubber, acrylonitrile rubber, polyurethane rubber, and polyisobutylene which either possess dry tack by themselves or develop such tack upon the addition of a plasticizer. The addition of certain PSA materials can be effective in lowering the plasticity of the elastomeric PSA composition. The optimum level of addition of the organic pressure sensitive adhesive materials will depend on the type used. In many instances, there is a level of addition above which the cure of the composition will be inhibited or the organic and silicone materials will phase separate.

The compositions may further include water-soluble hydrocolloid gums to provide wet tack and water absorbency, such as guar gum, karaya gum, locust bean gum, pectin, or mixtures thereof. For ostomy seal use, there may be a practical limit to the amount of hydrocolloids added, above which the cured elastomeric body may tend to erode and disintegrate in wet conditions. It is therefore thought that the hydrocolloids are best employed up to about 30% of the elastomeric PSA composition.

The compositions may further include pigments or reinforcing and extending fillers, such as fumed or precipitated silica or diatomaceous earth.

The elastomeric pressure sensitive adhesives may be made by mixing the ingredients in any order. However, it should be noted that upon addition of the catalyst to the combination of silanol-containing compounds and alkoxy containing compounds, curing may begin to take place. Specifically the pressure sensitive adhesives may be made by: (I) homogeneously mixing resin copolymer (A) and polydiorganosiloxane fluid (B), alkoxy-containing organosilicon compound (C), condensation catalyst (D), and, optionally, trimethyl-endblocked polydimethylsiloxane (E), (II) devolatilizing resin copolymer (A) optionally in mixture with other components so long as the mixture of resin copolymer (A) with the other components is substantially non-reactive at the temperature of devolatilization, (III) placing the elastomeric pressure sensitive adhesive composition in the desired form for curing, and (VI) curing the composition for a sufficient time to form the elastomeric pressure sensitive adhesive.

In one method of making the pressure sensitive adhesives, (a) resin copolymer (A) and polydiorganosiloxane fluid (B) are premixed and the premix is devolatized, (b) trimethyl-endblocked polydimethylsiloxane (E) is admixed to a portion of the premix, (c) organosilicon compound (C) is admixed to a portion of the premix, and (d) condensation catalyst (D) is admixed to a portion of the premix, where the portions may be the same or different and may each constitute from 0 to 100 percent of the total premix, (e) all the portions are homogeneously mixed together with any remaining portion of the premix, and then the composition is placed in the desired form for curing and cured.

The devolatization step (II) may be completed, for example, on the resin copolymer alone or on the resin copolymer in mixture with the polydiorganosiloxane fluid, the trimethyl-endblocked polydimethylsiloxane fluid, or both. In one preferred method, the devolatilization step is completed on the mixture of the resin copolymer, the polydiorganosiloxane fluid, and the trimethyl-endblocked polydimethylsiloxane fluid. If the volatile components are removed with heat, the procedure preferably includes the step of cooling the devolatilized resin copolymer, which is optionally in combination with other components, to room temperature before adding the crosslinker and the catalyst. If hydrocolloids or organic PSA materials are added to the composition, it is preferable that they be added before adding the catalyst to the combination of silanol-containing compounds and alkoxy-containing compounds, otherwise premature gellation may occur. The step of placing the composition into the desired form, as in step (V) above, can utilize any of many types of molding techniques, e.g. transfer, compression, extrusion, or injection molding.

In contrast with typical silicone gum-based pressure sensitive adhesives, removal of the volatile components as in step (II) is required for the preparation of the pressure sensitive adhesives of this invention. The devolatilization may be carried out at atmospheric pressure and temperatures up to about 200° C. or the devolatilization may be carried out under partial vacuum. Preferably, the devolatilization is carried out between 135° C. and 150° C.

Curing or vulcanization can be carried out at temperatures from room temperature to about 200° C. Initial curing or "setting" of the compositions are preferably hastened by heating for about one to 20 minutes. Optimum curing temperatures and times vary with the thickness of the molded body. Preferably, initial curing is carried out at about 100° C. for approximately 10 minutes, and the curing is allow to finish at room temperature. When this procedure is used, final physical properties of the elastomeric PSA will be achieved within 72 hours. During vulcanization, a volatile by-product is formed and must be allowed to escape in order to complete the curing. For example, when ethyl orthosilicate is used as the crosslinker, ethanol is formed by the reaction between the ethyl orthosilicate and the silanol groups on polydiorganosiloxane fluid (B), and this ethanol must be adequately removed to allow the reaction to go to completion. If slabs of elastomeric PSA's are being formed, the slabs are, preferably, press molded during the heating step to reduce the formation of bubbles or voids in the slab.

Mixing can be facilitated, if desired, by the addition of a mutual solvent as mentioned above. If solvent is used, the solvent is removed either during the devolatilization step (II) or during the curing step (VI).

When adding hydrocolloids or organic pressure sensitive adhesives, the materials are best blended with the other components before the addition of the catalyst.

The elastomeric pressure sensitive adhesive compositions may be stored in various ways. They may be stored as two-part systems, where one part contains the resin copolymer (A), the polydiorganosiloxane fluid (B), the organosilicon compound (C), and optionally other ingredients such as the trimethyl-endblocked polydimethylsiloxane (E), and the other part contains the catalyst (D) and optionally other ingredients. The compositions may also be stored as three-part systems, where one part contains the resin copolymer (A), the polydiorganosiloxane fluid (B), and optionally the trimethyl-endblocked polydimethylsiloxane (E), a second part contains the organosilicon compound (C) and a third part contains the catalyst (D). Various combinations of storing are feasible, so long as the catalyst is kept separate from the combination of silanol-containing compounds and the organosilicon compound (D) until use, otherwise, premature curing occurs.

The elastomeric pressure sensitive adhesives of this invention will adhere to many substrates such as paper, cloth, glass cloth, silicone rubber, polyethylene, polyethylene terephthalate, polytetrafluoroethylene, glass, wood, metals, and skin. Therefore, there are many uses for the elastomeric pressure sensitive adhesives of this invention, where a coating or a body of elastomeric pressure sensitive adhesive is desirable. For examples, uses such as tapes and medical adhesives, such as wound dressings and bandages or those adhesives used for sealing devices to the skin or for attaching prosthetic devices to the body are possible with the elastomeric PSA's of this invention.

For example, if a body of the cured elastomeric pressure sensitive adhesive is to be used to form a seal between the stoma of an ostomy patient and an attached appliance, the procedure would be to (a) form a body of elastomeric pressure sensitive adhesive using the composition as described herein, (b) attach the elastomeric pressure sensitive adhesive body on a patient's skin around the stoma, and (c) attach the appliance to the elastomeric pressure sensitive adhesive body.

The following examples are illustrative only and should not be construed as limiting the invention which is properly delineated in the appended claims. All parts and percentages are by weight and all viscosities are expressed at 25° C. unless otherwise specified.

Tack and adhesion values in the following examples were determined approximately three days after catalyst addition. Quantitative adhesion measurements reported herein were obtained through measuring the force required to peel a one-half inch wide 15 mil thick slab from a stainless steel panel by stripping at a rate of 12 inches/minute at an angle of 180°. Quantitative tack measurements were performed through the use of a POLYKEN TM brand Probe Tack Tester (Testing Machines, Inc., Amityville, N.Y.) on 15 ml. thick samples of the elastomeric PSA. Briefly summarized, tack measurements, expressed in units of grams/cm$^2$ of tack, were obtained using a probe velocity of 2 cm/sec., a contact pressure of 10 grams/cm$^2$, and a contact time of 10 seconds.

The silicon-bonded hydroxyl content was determined using a lithium aluminum hydride di-N-butyl amide titration based upon the one described by Kellum, et al., and Chem. 39,1623 ff (1967); see also Jorden, and Chem. 30,297 (1964).

The plasticities of the compositions were determined before addition of the crosslinker and catalyst using ASTM D926.

The amounts of non-volatile component (in percent) of the resin copolymers solutions were determined by first heating a 1.5 gram sample of the resin copolymer (A) for 2 hours at 150° C. in a forced draft oven, then calculating the percent non-volatile component by dividing the remaining weight of the sample after heating by the original weight of the sample.

In all of the examples, unless otherwise stated, curing was completed by press molding a slab of material at 100° C. for 10 minutes and then allowing the slab to finish curing at room temperature for 24–72 hours after catalyst addition.

In the following examples, Resin Copolymer A-1 is a xylene-soluble resin copolymer of 0.6 to 0.9 triorganosiloxane units per $SiO_{4/2}$ unit which contains silicon-bonded hydroxyl radicals which has been treated with hexamethyldisilazane to reduce the silicon-bonded hydroxyl content to less than 0.33 weight %. Resin Copolymer A-1 Solution is a xylene solution of Resin Copolymer A-1 having between 59 and 68 weight % non-volatile component.

Resin Copolymer A-2 is a xylene-soluble resin copolymer of 0.6 to 0.9 triorganosiloxane units per $SiO_{4/2}$ unit which contains from 2 to 4 weight % silicon-bonded hydroxyl radicals.

Siloxane Fluid B-1 is a hydroxyl-endblocked linear polydimethylsiloxane having a viscosity of about 70 cP.

Siloxane Fluid B-2 is a hydroxy-endblocked linear polydimethylsiloxane having a viscosity of about 2000 cP.

Siloxane Fluid B-3 is a hydroxy-endblocked linear polydimethylsiloxane having a viscosity of about 42 cSt.

EXAMPLE 1

685.4 g. of Resin Copolymer A-1 Solution and 270 g. of Siloxane Fluid B-1 were mixed together and heated to 110° C. until the xylene solvent was distilled out and the mixture was essentially 100% solids. The resulting distilled mixture consisted of 405 g. Resin Copolymer A-1 and 270 g. Siloxane Fluid B-1, and the plasticity of the distilled mixture was measured to be $49 \times 10^{-3}$ inches. 15.0 g. of the distilled mixture were mixed with 0.1 g. of Normal-propylorthosilicate crosslinker (hereinafter referred to as NPOS), 0.15 g. of a specially tested grade of stannous octoate, DOW CORNING ® Catalyst M (available from Dow Corning Corporation, Midland, MI), and 0.47 g. of 20 cSt. trimethyl-endblocked polydimethylsiloxane. The resulting product exhibited an adhesion of $184.9 +/- 24.6$ g/cm and a tack of $1261 +/- 134$ g/cm².

EXAMPLE 2

A distilled mixture of resin copolymer (A) and polydiorganosiloxane fluid (B) was prepared as in Example 1, except that Siloxane Fluid B-2 was used instead of Siloxane Fluid B-1. The resulting distilled mixture had a measured plasticity of $63 \times 10^{-3}$ inches. 45.0 g. of the distilled mixture were mixed with 0.47 g. of ethylpolysilicate crosslinker, 0.45 g. of DOW CORNING ® Catalyst M, and 1.42 g. of 20 cSt. trimethyl-endblocked polydimethylsiloxane. The resulting mixture was heated to 100° C. for 5 minutes to initiate curing and was then allowed to remain at room temperature for 72 hours to complete the curing. The resulting final adhesive product exhibited an adhesion of $435.9 +/- 70.3$ g/cm and a tack of $842 +/- 52.3$ g/cm².

EXAMPLES 3–5

These examples demonstrate that by using solely Resin Copolymer A-2, which has from 2 to 4 weight % silicon-bonded hydroxyl radicals, as the resin copolymer (A), the composition does not form an elastomer with pressure sensitive adhesive properties. The compositions of examples 3–5 are given in Table 1. The cellulose gum used was Cellulose Gum Type 7HO48F which is a high viscosity, food-grade sodium carboxymethylcellulose having an average of 7 carboxymethyl groups per 10 anhydro-glucose units supplied by Hercules, Inc., Wilmington, Del. "Elastomer Base E" consisted of 44 weight % of Resin Copolymer A-2, 36 weight % of Siloxane Fluid B-1, and 20 weight % of a polydimethylcyclosiloxane fluid. The polydimethylcyclosiloxane fluid used was a mixture of cyclic compound predominantly having from 3 to 6 dimethylsiloxane units. The compositions for examples 3–5 when cured exhibited no tack and therefore were not pressure sensitive adhesives.

TABLE 1

| Ingredient | Weight of Ingredient (g.) | | |
|---|---|---|---|
| | Example 3 | Example 4 | Example 5 |
| Cellulose gum | 3 | 3 | 0 |
| Elastomer Base A | 17 | 17 | 8.55 |
| Siloxane Fluid B-3 | 0.32 | 0.32 | 0 |
| Stannous Octoate | 0.5 | 1.0 | 0.45 |
| NPOS | 0.23 | 0.19 | 0 |

EXAMPLES 6–10

Examples 6–10 demonstrate the results on adhesion and tack of varying the resin copolymer (A) to siloxane fluid (B) ratio between 51:49 and 60:40. Table 2 provides the compositions for Examples 6–10. For these examples, 4158.64 g. of Resin Copolymer A-1 Solution (which was 59.09% non-volatile component) was mixed with 1637.83 g. of Siloxane Fluid B-1. The mixture was heated and vacuum stripped to remove the volatile components. Then 126.65 g. of 20 cSt. trimethyl-endblocked polydimethylsiloxane (PDMS) was added to the stripped mixture to form "Elastomer Base B" which had about a 60:40 weight ratio of resin copolymer (A) to siloxane fluid (B). The tack and adhesion properties of the cured products are given in Table 3.

TABLE 2

| Ingredient | Weight of Ingredient (g.) | | | | |
|---|---|---|---|---|---|
| | Example 6 | Example 7 | Example 8 | Example 9 | Example 10 |
| Elastomer Base B | 15.0 | 15.0 | 15.0 | 15.0 | 15.0 |

TABLE 2-continued

| Ingredient | Weight of Ingredient (g.) | | | | |
|---|---|---|---|---|---|
| | Example 6 | Example 7 | Example 8 | Example 9 | Example 10 |
| Siloxane Fluid B-1 | 0.0 | 0.82 | 1.39 | 2.0 | 2.65 |
| NPOS | 0.1 | 0.11 | 0.12 | 0.13 | 0.14 |
| DOW CORNING ® Catalyst M | 0.2 | 0.2 | 0.2 | 0.2 | 0.2 |
| 20 cSt. PDMS | 0.0 | 0.05 | 0.07 | 0.09 | 0.11 |

TABLE 3

| Example # | Weight Ratio of Resin Copolymer (A) to Siloxane Fluid (B) | Adhesion (g/cm) | Tack (g/cm²) |
|---|---|---|---|
| 6 | 60/40 | 167.6 | 1298 |
| 7 | 57/43 | 65.03 | 787 |
| 8 | 55/45 | 39.72 | 634 |
| 9 | 53/47 | 27.77 | 480 |
| 10 | 51/49 | 24.96 | 442 |

EXAMPLES 11-14

Examples 11-14 demonstrate the results on adhesion of varying the resin copolymer (A) to polydiorganosiloxane fluid (B) ratio between 60/40 and 66/34.

In these examples, freon was added to the formulation to allow the formulation to be laminated for testing. These compositions without the freon, however, would be moldable. For these examples, "Elastomer Base C" was prepared by blending 1259.95 g. of Resin Copolymer A-1 Solution (62.78 weight % non-volatile component) with 339.0 g. of Siloxane Fluid B-1 and heating to 145° C. with a nitrogen sweep to drive off the xylene solvent.

For example 11, 100 g. of Elastomeric Base C was mixed with 16.67 g. of Siloxane Fluid B-1 resulting in a composition having a 60/40 weight ratio of resin copolymer (A) to polydiorganosiloxane fluid (B). 50 g. of this mixture was blended with 77.78 g. of freon and 0.2 g. of NPOS. For example 12, 100 g. of Elastomer Base C was mixed with 12.9 g. of Siloxane Fluid B-1 resulting in a composition having a 62/38 weight ratio of resin copolymer (A) to polydiorganosiloxane fluid (B). 50 g. of this mixture was blended with 75.27 g. of freon and 0.19 g. of NPOS. For example 13, 100 g. of Elastomer Base C was mixed with 9.38 g. of Siloxane Fluid B-1 resulting in a composition having a 64/36 weight ratio of resin copolymer (A) to polydiorganosiloxane fluid (B). 50 g. of this mixture was blended with 72.92 g. of freon and 0.18 g. of NPOS. For example 14, 100 g. of Elastomer Base C was mixed with 6.06 g. of Siloxane Fluid B-1 resulting in a composition having a 66/34 weight ratio of resin copolymer (A) to polydiorganosiloxane fluid (B). 50 g. of this mixture was blended with 70.71 g. of freon and 0.17 g. of NPOS. The compositions were allowed to cure at room temperature, and after about 3 days, adhesion of the cured samples was determined and the results are given in Table 4.

TABLE 4

| Example # | Weight Ratio of Resin Copolymer (A) to Siloxane Fluid (B) | Adhesion (g/cm) |
|---|---|---|
| 11 | 60/40 | 414.5 ± 61.5 |
| 12 | 62/38 | 484.4 ± 7.03 |
| 13 | 64/36 | 7.031 ± 3.16 |
| 14 | 66/34 | 6.679 ± 1.7 |

EXAMPLES 15-19

Examples 15-19 exhibit the results on adhesion and tack of substituting Resin Copolymer A-2 for part of Resin Copolymer A-1. For these examples, "Elastomer Base D" was prepared by blending 683.59 g. of Resin Copolymer A-1 Solution (59.09% non-volatile component) with 268.1 g. of Siloxane Fluid B-1 and heating without vacuum to remove the volatile components. The resulting Elastomer Base D was 60.11% resin copolymer (A) and 39.89% polydiorganosiloxane fluid (B). Elastomer Base D had a measured plasticity value of $49 \times 10^{-3}$ inches.

"Elastomer Base E" was prepared by blending 587.8 g. of Resin Copolymer A-2 Solution (68.9 weight percent Resin Copolymer A-2 in solvent) and 270 g. of Siloxane Fluid B-1, and 20 cSt. trimethyl-endblocked polydimethylsiloxane. The solvent was removed from the resulting blend and the final Elastomer Base E was 57.86 weight percent Resin Copolymer A-2, 38.57 weight percent Siloxane Fluid B-1, and 3.57 weight percent 20 cSt. trimethyl-endblocked polydimethylsiloxane. The compositions used for these examples are detailed in Table 5 below. The tack and adhesion of the cured compositions are given in Table 6.

TABLE 5

| Ingredient | Example 15 | Example 16 | Example 17 | Example 18 | Example 19 |
|---|---|---|---|---|---|
| Elastomer Base D | 15.0 | 15.0 | 15.0 | 15.0 | 15.0 |
| Elastomer Base E | 0.0 | 0.52 | 1.03 | 1.67 | 2.308 |
| NPOS | 0.1 | 0.11 | 0.12 | 0.13 | 0.14 |
| 20 cSt. PDMS | 0.47 | 0.49 | 0.50 | 0.52 | 0.54 |
| Catalyst M | 0.2 | 0.2 | 0.2 | 0.2 | 0.2 |

TABLE 6

| Example # | Resin Copolymer A-2 in Composition (percent) | Adhesion (g/cm) | Tack (g/cm²) |
|---|---|---|---|
| 15 | 0 | 185 | 1261 |
| 16 | 1.7 | 126 | 1133 |
| 17 | 3.7 | 101 | 951 |
| 18 | 5.7 | 83 | 1121 |
| 19 | 7.7 | 81 | 999 |

EXAMPLES 20-24

Examples 20-24 demonstrate the effects of varying the amount of trimethyl-endblocked polydimethylsiloxane added to the elastomeric PSA composition.

For each example, 15.0 g. of Elastomer Base B was blended with 0.1 g. of NPOS, and 0.2 g. of Catalyst M. For example 20, no additional trimethyl-endblocked polydimethylsiloxane fluid was added resulting in a composition including about 3 weight % trimethyl-endblocked polydimethylsiloxane fluid. For example 21, 0.53 g. of a trimethyl-endblocked polydimethylsiloxane fluid having a viscosity of 100 cSt. (hereinafter referred to as 100 cSt. PDMS) was added to the blend resulting in a composition including about 6 weight % PDMS. For example 22, 1.06 g. of 100 cSt. PDMS was added to result in about 9 weight % PDMS, for example 23, 1.64 g. of 100 cSt. PDMS was added to result in about 12 weight % PDMS, and for example 24, 2.25 g. of 100 cSt. PDMS was added to result in about 15 weight % PDMS in the blend. The compositions of examples 20 and 21 were not easily flowable, however, the composition of example 22 was movable with air pressure (about 90 psi), example 23 was self-levelling, and example 24 was very flowable.

The tack and adhesion properties of these cured products are given in Table 7.

TABLE 7

| Example # | Trimethyl-endblocked polydimethylsiloxane (Weight %) | Adhesion (g/cm) | Tack (g/cm 2) |
|---|---|---|---|
| 20 | 3 | 177 | 1148 |
| 21 | 6 | 78 | 927 |
| 22 | 9 | 55 | 894 |
| 23 | 12 | 26 | 690 |
| 24 | 15 | 54 | 480 |

These and other variations of the present invention may be made which fall within the scope of the appended claims even though such variations were not specifically discussed above.

That which is claimed is:

1. A composition for forming elastomeric pressure sensitive adhesives comprising a homogeneous mixture of:
   (A) a xylene-soluble resin copolymer employed in an amount from 50 to 70 parts by weight, said xylene-soluble resin copolymer consisting essentially of $R_3SiO_{\frac{1}{2}}$ units and $SiO_{4/2}$ units in a mol ratio of from 0.6 to 0.9 $R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units, said resin copolymer substantially free of volatile components,
   (B) a polydiorganosiloxane fluid employed in an amount from 30 to 50 parts by weight, said polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity such that the elastomeric pressure sensitive adhesive composition has a plasticity of less than $150 \times 10^{-3}$ inches at 25° C. without the addition of organic solvents, the total of resin copolymer (A) and polydiorganosiloxane fluid (B) being 100 parts by weight,
   (C) an alkoxy-containing organosilicon compound having an average of more than two silicon-bonded alkoxy units per molecule employed in an amount from 0.35 to 2 parts by weight,
   (D) a condensation catalyst employed in an amount from 0.5 to 13 parts by weight, and
   (E) a trimethyl-endblocked polydimethylsiloxane employed from 0 to 15 parts by weight and having a viscosity of from 10 to 1000 cSt. at 25° C.

2. A composition for forming elastomeric pressure sensitive adhesives comprising a homogeneous mixture of:
   (A) a xylene-soluble resin copolymer employed in an amount from 50 to 70 parts by weight, said xylene-soluble resin copolymer consisting essentially of $R_3SiO_{\frac{1}{2}}$ units and $SiO_{4/2}$ units in a mol ratio of from 0.6 to 0.9$R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units, said resin copolymer substantially free of volatile components,
   (B) a polydiorganosiloxane fluid employed in an amount from 30 to 50 parts by weight, said polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity of from 50 to 300,000 cP. at 25° C., the total of resin copolymer (A) and polydiorganosiloxane fluid (B) being 100 parts by weight,
   (C) an alkoxy-containing organosilicon compound having an average of more than two silicon-bonded alkoxy units per molecule employed in amount from 0.35 to 2 parts by weight, and
   (D) a condensation catalyst employed in an amount from 0.5 to 13 parts by weight.

3. The composition as claimed in claim 2 further comprising an organic solvent.

4. The composition as claimed in claim 2 further comprising an organic material selected from the group consisting of natural rubber, styrene-butadiene rubber, acrylonitrile rubber, polyurethane rubber, and polyisobutylene.

5. The composition as claimed in claim 2 further comprising a hydrocolloid.

6. The composition as claimed in claim 5 wherein the hydrocolloid is present in an amount less than 30 weight percent based on the weight of the composition for forming elastomeric pressure sensitive adhesives.

7. The composition as claimed in claim 2 further comprising from 0 to 15 parts by weight of a trimethyl-endblocked polydimethylsiloxane having a viscosity of from 10 to 1000 cSt. at 25° C.

8. The composition as claimed in claim 2 wherein said xylene-soluble resin copolymer is employed from 58 to 62 parts by weight and said polydiorganosiloxane fluid is employed from 38 to 42 parts by weight.

9. The composition as claimed in claim 8 wherein said resin copolymer has less than 0.33 weight % silicon-bonded hydroxyl units and said polydiorganosiloxane fluid has a viscosity of from 50 to 5000 cP at 25° C. and R' is a methyl radical.

10. The composition as claimed in claim 9 wherein said polydiorganosiloxane fluid has a viscosity of from 50 to 100 cP at 25° C.

11. The composition as claimed in claim 10 wherein said alkoxy-containing organosilicon compound is N-propyl orthosilicate and is employed from 0.67 to 1.33 parts by weight based on the total weight of the resin copolymer and the polydiorganosiloxane fluid.

12. The composition as claimed in claim 11 wherein said condensation catalyst is stannous octoate.

13. A kit for making a pressure sensitive adhesive comprising:
a first package containing a homogeneous mixture of
(A) a xylene-soluble resin copolymer in an amount from 50 to 70 parts by weight, said xylene-soluble resin copolymer consisting essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units, said resin copolymer substantially free of volatile components, and
(B) 30 to 50 parts by weight of a polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity of from 50 to 300,000 cP. at 25° C., the total of resin copolymer (A) and polydiorganosiloxane fluid (B) being 100 parts by weight,
a second package containing
(C) an alkoxy-containing organosilicon compound having an average of more than two silicon-bonded alkoxy units per molecule in an amount from 0.35 to 2 parts by weight, and
a third package containing
(D) a condensation catalyst in an amount from 0.5 to 13 parts by weight.

14. A kit for making a pressure sensitive adhesive comprising:
a first package containing a homogeneous mixture of
(A) a xylene-soluble resin copolymer in an amount from 50 to 70 parts by weight, said xylene-soluble resin copolymer consisting essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units, said resin copolymer substantially free of volatile components,
(B) 30 to 50 parts by weight of a polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity of from 50 to 300,000 cP. at 25° C., the total of resin copolymer (A) and polydiorganosiloxane fluid (B) being 100 parts by weight, and
(C) an alkoxy-containing organosilicon compound having an average of more than two silicon-bonded alkoxy units per molecule in an amount from 0.35 to 2 parts by weight and
a second package containing
(D) a condensation catalyst in an amount from 0.5 to 13 parts by weight.

15. The cured composition formed from the composition of claim 1.

16. The cured composition formed from the composition of claim 2.

17. The cured composition formed from the composition of claim 4.

18. The cured composition formed from the composition of claim 5.

19. The cured composition formed from the composition of claim 12.

20. A method of forming a silicone elastomeric pressure sensitive adhesive comprising the steps of:
(i) preparing an elastomeric pressure sensitive adhesive composition by
(I) homogeneously mixing
(A) 50 to 70 parts by weight of a xylene-soluble resin copolymer consisting essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units,
(B) 30 to 50 parts by weight of a polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity such that the elastomeric pressure sensitive adhesive composition has a plasticity of less than $150 \times 10^{-3}$ inches at 25° C. without the addition of organic solvents, the total of resin copolymer (A) and polydiorganosiloxane fluid (B) being 100 parts by weight,
(C) an alkoxy-containing organosilicon compound having an average of more than two silicon-bonded alkoxy units per molecule in an amount from 0.35 to 2 parts by weight,
(D) a condensation catalyst in an amount from 0.5 to 13 parts by weight, and
(E) no more than 15 parts by weight of a trimethyl-endblocked polydimethylsiloxane having a viscosity of from 10 to 1000 cSt. at 25° C., and
(II) devolatilizing said resin copolymer
(A) optionally in mixture with other components wherein the mixture of resin copolymer (A) with other components is substantially nonreactive at the temperature of devolatilization,
(ii) placing the elastomeric pressure sensitive adhesive composition in the desired form for curing, and
(iii) curing the composition which has been placed in the desired form for curing for a sufficient time to form the elastomeric pressure sensitive adhesive.

21. The method as claimed in claim 20 wherein step (I) comprises the steps of:
(a) mixing said resin copolymer (A) and said polydiorganosiloxane fluid (B),
(b) admixing said trimethyl-endblocked polydimethylsiloxane (E) to a first portion of the mixture of resin copolymer (A) and polydiorganosiloxane fluid (B),
(c) admixing said organosilicon compound (C) to a second portion of the mixture of resin copolymer (A) and polydiorganosiloxane fluid (B), (d) admixing said condensation catalyst (D) to a third portion of the mixture of resin copolymer (A) and polydiorganosiloxane fluid (B), wherein said portions may be the same or different and may each be from 0 to 100 percent of the mixture of resin copolymer (A) and polydiorganosiloxane fluid (B), and (e) homogeneously mixing said first, second, and third portions together with any remaining portion of the mixture of resin copolymer (A) and polydiorganosiloxane fluid (B), and step (II) is carried out after step (a) and before steps (c) and (d).

22. A method of forming a silicone elastomeric pressure sensitive adhesive comprising the steps of:
   (i) preparing an elastomeric pressure sensitive adhesive composition by
      (I) homogeneously mixing
         (A) 50 to 70 parts by weight of a xylene-soluble resin copolymer consisting essentially of $R_3SiO_{\frac{1}{2}}$ units and $SiO_{4/2}$ units in a mol ratio of from 0.6 to $0.9R_3SiO_{\frac{1}{2}}$ units for each $SiO_{4/2}$ unit, wherein each R denotes, independently, a monovalent hydrocarbon radical having from 1 to 6 inclusive carbon atoms, said resin copolymer having less than 0.7 weight % silicon-bonded hydroxyl units,
         (B) 30 to 50 parts by weight of a polydiorganosiloxane fluid endcapped with silicon-bonded hydroxyl groups and having the average formula $HO(R'_2SiO)_nH$ wherein each R' denotes, independently, a monovalent hydrocarbon or halohydrocarbon radical having from 1 to 6 inclusive carbon atoms and n has an average value so that the polydiorganosiloxane fluid has a viscosity of from 50 to 300,000 cP. at 25° C., the total of resin copolymer (A) and polydiorganosiloxane fluid (B) being 100 parts by weight, and
         (C) an alkoxy-containing organosilicon compound having an average of more than two silicon-bonded alkoxy units per molecule in an amount from 0.35 to 2 parts by weight,
         (D) a condensation catalyst in an amount from 0.5 to 13 parts by weight,
         (E) 0 to 15 parts by weight of a trimethyl-endblocked polydimethylsiloxane having a viscosity of from 10 to 1000 cSt. at 25° C., and
      (II) devolatilizing said resin copolymer (A) optionally in mixture with other components wherein said mixture of resin copolymer (A) with other components is substantially non-reactive at the temperature of devolatilization,
   (ii) placing the elastomeric pressure sensitive adhesive composition in the desired form for curing, and
   (iii) curing the composition which has been placed in the desired form for curing for a sufficient time to form the elastomeric pressure sensitive adhesive.

23. The method as claimed in claim 22 wherein step (I) comprises the steps of:
   (a) mixing said resin copolymer (A) and said polydiorganosiloxane fluid (B),
   (b) admixing said trimethyl-endblocked polydimethylsiloxane (E) to a first portion of the mixture of resin copolymer (A) and polydiorganosiloxane fluid (B),
   (c) admixing said organosilicon compound (C) to a second portion of the mixture of resin copolymer (A) and polydiorganosiloxane fluid (B),
   (d) admixing said condensation catalyst (D) to a third portion of the mixture of resin copolymer (A) and polydiorganosiloxane fluid (B), wherein said portions may be the same or different and may each be from 0 to 100 percent of the mixture of resin copolymer (A) and polydiorganosiloxane fluid (B), and (e) homogeneously mixing said first, second, and third portions together with any remaining portion of the mixture of resin copolymer (A) and polydiorganosiloxane fluid (B), and step (II) is carried out after step (a) and before steps (c) and (d).

* * * * *